United States Patent

Friebe et al.

[11] 3,996,361
[45] Dec. 7, 1976

[54] N⁶-SUBSTITUTED-9-[3-(4-PHENYL-PIPERAZINO)-PROPYL]-ADENINES

[75] Inventors: Walter-Gunar Friebe, Darmstadt; Max Thiel, Mannheim; Werner Winter, Viernheim; Androniki Roesch, Mannheim; Wolfgang Schaumann, Heidelberg, all of Germany

[73] Assignee: Boehringer Mannheim G.m.b.H., Mannheim, Germany

[22] Filed: Dec. 10, 1974

[21] Appl. No.: 531,420

[30] Foreign Application Priority Data

Jan. 11, 1974 Germany .................. 2401254

[52] U.S. Cl. .................. 424/253; 260/252; 260/253
[51] Int. Cl.² .................. C07D 473/34
[58] Field of Search .......... 260/252, 253; 424/253

[56] References Cited

UNITED STATES PATENTS

| | | | |
|---|---|---|---|
| 3,457,263 | 7/1969 | Regnier et al. | 260/252 |
| 3,862,189 | 1/1975 | Schwender | 260/252 |
| 3,917,596 | 11/1975 | Winter et al. | 260/252 |

FOREIGN PATENTS OR APPLICATIONS

| 621,979 | 2/1963 | Belgium | 260/252 |
|---|---|---|---|

Primary Examiner—Paul M. Coughlan, Jr.
Attorney, Agent, or Firm—Burgess, Dinklage & Sprung

[57] ABSTRACT

A N⁶-substituted-9-[3-(4-phenyl-piperazino)-propyl]-adenine of the formula

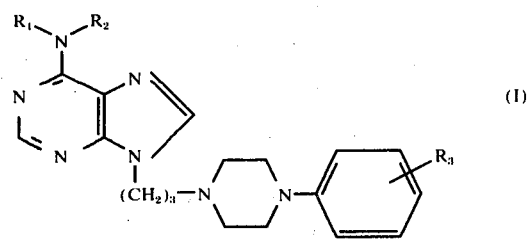

(I)

wherein
  $R_1$ is hydrogen or a lower alkyl radical, and
  $R_2$ is a lower alkyl radical, a lower alkyl radical substituted by at least one of phenyl and hydroxyl, a lower alkenyl radical, a cycloalkyl radical or an aryl radical, or
  $R_1$ and $R_2$ together with the nitrogen atom to which they are attached form a piperidine, pyrrolidine or morpholine ring, and
  $R_3$ is hydrogen, halogen, a lower alkyl radical or a lower alkoxy radical,
or a salt thereof with a pharmacologically compatible acid, which compounds are characterized by marked anti-edematous activity as well as by activity in reducing capillary permeability.

9 Claims, No Drawings

N⁶-SUBSTITUTED-9-[3-(4-PHENYL-PIPERAZINO)-PROPYL]-ADENINES

The present invention is concerned with new arylpiperazine derivatives of adenine and with the preparation thereof.

The new aryl-piperazine derivatives of adenine according to the present invention are compounds of the general formula

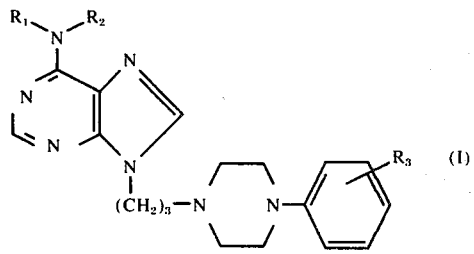

wherein
- $R_1$ is hydrogen or a lower alkyl radical, and
- $R_2$ is a lower alkyl radical, a lower alkyl radical substituted by at least one of phenyl and hydroxyl, a lower alkenyl radical, a cycloalkyl radical or an aryl radical, or
- $R_1$ and $R_2$ together with the nitrogen atom to which they are attached from a piperidine, pyrrolidine or morpholine ring, and
- $R_3$ is hydrogen, halogen, a lower alkyl radical or a lower alkoxy radical, or a salt thereof with a pharmacologically compatible acid.

We have found that the new compounds of general formula (I) have an anti-edematous action and reduce capillary permeability. They can suppress the liberation and the action of histamine and serotonin and thus have an anti-inflammatory and anti-allergic action.

The new compounds according to the present invention can be prepared, for example, by one of the following methods:

a. reaction of a N⁶-substituted adenine of the general formula:

wherein $R_1$ and $R_2$ have the same meanings as above, with an aryl-piperazine derivative of the general formula:

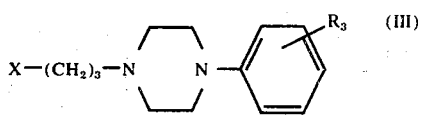

wherein $R_3$ has the same meaning as above and X represents a reactive residue; or b. reaction of a purine derivative of the general formula:

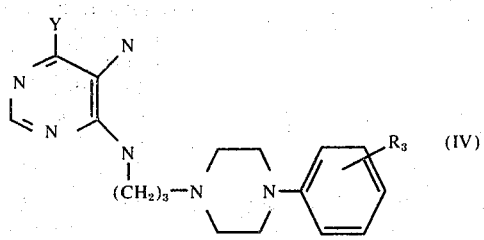

wherein $R_3$ has the same meaning as above, and Y is a reactive residue, or an acid-addition salt thereof, with an amine of the general formula:

$$R_1 - NH - R_2 \quad (V)$$

wherein $R_1$ and $R_2$ have the same meanings as above; whereafter, if desired, the product obtained is converted into a pharmacologically compatible salt.

The lower alkyl radicals of the substituents $R_1$, $R_2$ and $R_3$ can be straight-chained or branched and contain up to 6 and preferably up to 4 carbon atoms. Preferably the lower alkenyl radicals contain 2 to 4 carbon atoms, the cycloalkyl radicals contain 3 to 6 carbon atoms and the lower alkoxy radicals contain up to 4, especially up to 3 carbon atoms.

The halogen atoms are preferably fluorine, chlorine or bromine atoms.

The reactive residue X can be, for example, a chlorine or bromine atom or a mesyloxy or tosyloxy radical.

The reaction of the adenine derivative of general formula (II) with the compound of general formula (III) preferably takes place in an alkaline medium and more preferably in a lower alcohol, for example isopropanol, in the presence of sodium isopropylate. Under these conditions, in addition to the compounds of general formula (I), small amounts of the isomeric derivatives substituted in the 7-position are also obtained which can, however, easily be removed by simple recrystallization of the reaction products. With regard to the 9-substitution of adenine in an alkaline medium, see also page 342 of "The Chemistry of Heterocyclic Compounds": Fused Pyrimidines, Part II, Purines, published by Wiley-Interscience.

As reactive residues Y, there can be used, for example, halogen atoms or alkylthio or benzylthio radicals.

When Y is a halogen atom, the reaction is preferably carried out in a solvent, such as dioxane, or in a lower alcohol, at boiling temperature.

When Y is an alkylthio or benzylthio radical, higher temperatures are necessary for the reaction; it is best to work with excess amine of general formula (V) as solvent, preferably at a temperature of 130° – 150° C, and, if necessary, in an autoclave.

The compounds of general formulae (II), (III), and (IV) are either known compounds or can readily be prepared from known compounds using conventional methods.

The pharmacologically compatible salts can be obtained in conventional manner, for example, by neutralization of compounds of general formula (I) with non-toxic inorganic or organic acids, for example, hydrochloric acid, sulfuric acid, phosphoric acid, hydrobromic acid, acetic acid, lactic acid, citric acid, malic acid, salicylic acid, malonic acid, maleic acid or succinic acid.

The new compounds of general formula (I) according to the present invention and the salts thereof can be administered enterally and parenterally in liquid or solid form. For this purpose, there can be used all the conventional forms of administration, for example, tablets, capsules, dragees, syrups, solutions, suspensions and the like. As injection medium, it is preferred to use water which contains the usual additives for injection solutions, such as stabilizing agents, solubilizing agents and buffers. Additives of this type include, for example, tartrate and citrate buffers, ethanol, complex-forming agents such as ethylenediamine-tetraacetic acid and the non-toxic salts thereof, and high molecular weight polymers such as liquid polyethylene oxide for viscosity regulation. Liquid carrier materials for injection solutions must be sterile and are preferably placed into ampules. Solid carrier materials include, for example, starch, lactose mannitol, methyl cellulose, talc, highly dispersed silicic acids, high molecular weight fatty acids such as stearic acid, gelatine, agar-agar, calcium phosphate, magnesium stearate, animal and vegetable fats, and solid high molecular weight polymers such as polyethylene glycols. Compositions suitable for oral administration can, if desired, contain flavoring and sweetening agents.

The following Examples are given for the purpose of illustration the present invention:

Example 1 a. $N^6$-Methyl-9-[3-(4-phenyl-piperazino)-propyl]-adenine.

1.38 g (0.06 mole) of sodium are dissolved in 120 ml of isopropanol. 8.9 g (0.06 mole) of $N^6$-methyl-adenine are added to this solution, which is then heated under reflux for 10 minutes, cooled and 15.8 g (0.066 mole) of 3-(4-phenyl-piperazino)-propyl chloride in 30 ml of isopropanol are added thereto. This reaction mixture is heated under reflux for 6 hours. Thereafter, it is cooled, suction filtered and sodium chloride washed out from the residue with water. After washing with water and drying, the product is recrystallized from isopropanol. There are obtained 9.5 g (45% of theory) of $N^6$-methyl-9-[3-(4-phenyl-piperazino)-propyl]-adenine, which has a melting point of 162°–163° C.

The following compounds are prepared in an analogous manner:

b. $N^6$-methyl-9-{3-[4-(3-chlorophenyl)-piperazino]-propyl}-adenine from $N^6$-methyl-adenine and 3-[4-(3-chlorophenyl)-piperazino]-propyl chloride; yield 52% of theory; m.p. 103°–104° C after recrystallization from isopropanol;

c. $N^6$-methyl-9-{3-[4-(2-methoxyphenyl)-piperazino]-propyl}-adenine from $N^6$-methyl-adenine and 3-[4-(2-methoxyphenyl)-piperazino]-propyl chloride; yield 50% of theory; m.p. 150°–151° C after recrystallization from ethyl acetate;

d. $N^6$-ethyl-9-[3-(4-phenyl-piperazino)-propyl]-adenine from $N^6$-ethyl-adenine and 3-(4-phenyl-piperazino)-propyl chloride; yield 45% of theory; m.p. 95°–96° C after recrystallization from cyclohexane;

e. $N^6$-tert.-butyl-9-[3-(4-phenyl-piperazino)-propyl]-adenine from $N^6$-tert.-butyl-adenine and 3-(4-phenyl-piperazino)-propyl chloride; yield 61% of theory; m.p. of dihydrochloride 245°–247° C after recrystallization from isopropanol;

f. $N^6$-allyl-9-[3-(4-phenyl-piperazino)-propyl]-adenine from $N^6$-allyl-adenine and 3-(4-phenyl-piperazino)-propyl chloride; yield 51% of theory; m.p. of the dihydrochloride 270°–272° C after recrystallization from ethanol;

g. $N^6$-phenyl-9-[3-(4-phenyl-piperazino)-propyl]-adenine from $N^6$-phenyl-adenine and 3-(4-phenyl-piperazino)-propyl chloride; yield 49% of theory; m.p. 128°–129° C after recrystallization from isopropanol;

h. $N^6$-benzyl-9-[3-(4-phenyl-piperazino)-propyl]-adenine from $N^6$-benzyl-adenine and 3-(4-phenyl-piperazino)-propyl chloride; yield 60% of theory; m.p. 95°–96° C after recrystallization from isopropanol;

i. d-$N^6$-(1-phenyl-isopropyl)-9-[3-(4-phenyl-piperazino)-propyl]-adenine from d-$N^6$-(1-phenyl-isopropyl)-adenine and 3-(4-phenyl-piperazino)-propyl chloride; yield 45% of theory; m.p. of the dihydrochloride 241°–242° C after recrystallization from methanol;

j. dl-$N^6$-(1-phenyl-isopropyl)-9-[3-(4-phenyl-piperazino)-propyl]-adenine from dl-$N^6$-(1-phenyl-isopropyl)-adenine and 3-(4-phenyl-piperazino)-propyl chloride; yield 92% of theory; m.p. of the dihydrochloride 216°–218° C after recrystallization from methanol;

k. dl-erythro-$N^6$-(1-hydroxy-1-phenyl-isopropyl)-9-[3-(4-phenyl-piperazino)-propyl]-adenine from dl-erythro-$N^6$-(1-hydroxy-1-phenyl-isopropyl)-adenine and 3-(4-phenylpiperazino)-propyl chloride; yield 63% of theory; m.p. of the dihydrochloride 243°–246° C after recrystallization from ethanol;

l. $N^6$-dimethyl-9-[3-(4-phenyl-piperazino)-propyl]-adenine from $N^6$-dimethyl-adenine and 3-(4-phenyl-piperazino)-propyl chloride; yield 43% of theory; m.p. 80°–81° C after recrystallization from isopropanol;

m. $N^6$-dimethyl-9-{3-[4-(3-chlorophenyl)-piperazino]-propyl}-adenine from $N^6$-dimethyl-adenine and 3-[4-(3-chlorophenyl)-piperazino]-propyl chloride; yield 61% of theory; m.p. 92°–93° C after recrystallization from isopropanol;

n. $N^6$-diethyl-9-[3-(4-phenyl-piperazino)-propyl]-adenine from $N^6$-diethyl-adenine and 3-(4-phenyl-piperazino)-propyl chloride; yield 60% of theory; m.p. of the dihydrochloride 256°–257° C after recrystallization from ethanol;

o. 6-piperidino-9-[3-(4-phenyl-piperazino)-propyl]-purine from 6-piperidino-purine and 3-(4-phenyl-piperazino)-propyl chloride; yield 47% of theory; m.p. of the dihydrochloride 261°–263° C after recrystallization from ethanol;

p. 6-morpholino-9-[3-(4-phenyl-piperazino)-propyl]-purine from 6-morpholino-purine and 3-(4-phenyl-piperazino)-propyl chloride; yield 43% of theory; m.p. 93°–95° C after recrystallization from ethyl acetate;

q. $N^6$-methyl-9-{3-[4-(4-fluorophenyl)-piperazino]-propyl}-adenine from $N^6$-methyl-adenine and 3-[4-(4-fluorophenyl)-piperazino]-propyl chloride; yield 59% of theory; m.p. 154°–155° C after recrystallization from ethyl acetate;

r. $N^6$-methyl-9-{3-[4-(4-methoxy-phenyl)-piperazino]-propyl}-adenine from $N^6$-methyl-adenine and 3-[4-(4-methoxy-phenyl)-piperazino]-propyl chloride; yield 46% of theory; m.p. 136°–138° C after recrystallization from ethanol;

s. $N^6$-methyl-9-{3-[4-(2-methylphenyl)-piperazino]-propyl}-adenine from $N^6$-methyl-adenine and 3-[4-(2-methylphenyl)-piperazino]-propyl chloride; yield 67% of theory; m.p. 133°–134° C after recrystallization from ethyl acetate;

t. $N^6$-cyclopropyl-9-[3-(4-phenyl-piperazino)-propyl]-adenine from $N^6$-cyclopropyl-adenine and 3-(4-phenyl-piperazino)-propyl chloride; yield 41% of theory; m.p. 129°–131° C after recrystallization from ethyl acetate;

u. $N^6$-cyclohexyl-9-[3-(4-phenyl-piperazino)-propyl]-adenine from $N^6$-cyclohexyl-adenine and 3-(4-phenyl-piperazino)-propyl chloride; yield 58% of theory; m.p. of the dihydrochloride 278°–281° C after recrystallization from methanol;

v. 6-pyrrolidino-9-[3-(4-phenyl-piperazino)-propyl]-purine from 6-pyrrolidino-purine and 3-(4-phenyl-piperazino)-propyl chloride; yield 47% of theory; m.p. 114°–115° C after recrystallization from ethyl acetate;

w. $N^6$-methyl-9-{3-[4-(3-methoxyphenyl)-piperazino]-propyl}-adenine from $N^6$-methyl-adenine and 3-[4-(3-methoxyphenyl)-piperazino]-propyl chloride; yield 47% of theory; m.p. 132°–133° C after recrystallization from ethyl acetate;

x. $N^6$-methyl-9-{3-[4-(3-methylphenyl)-piperazino]-propyl}-adenine from $N^6$-methyl-adenine and 3-[4-(3-methylphenyl)-piperazino]-propyl chloride; yield 63% of theory; m.p. 120°–121° C after recrystallization from ethyl acetate;

y. $N^6$-methyl-9-{3-[4-(4-methylphenyl)-piperazino]-propyl}-adenine from $N^6$-methyl-adenine and 3-[4-(4-methylphenyl)-piperazino]-propyl chloride; yield 58% of theory; m.p. 167°–169° C after recrystallization from isopropanol;

z. $N^6$-ethyl-9-{3-[4-(3-chlorophenyl)-piperazino]-propyl}-adenine from $N^6$-ethyl-adenine and 3-[4-(3-chlorophenyl)-piperazino]-propyl chloride; yield 42% of theory; m.p. 110°–111° C after recrystallization from ethyl acetate;

aa. $N^6$-isopropyl-9-[3-(4-phenyl-piperazino)-propyl]-adenine from $N^6$-isopropyl-adenine and 3-(4-phenyl-piperazino)-propyl chloride; yield 45% of theory; m.p. 76°–77° C after recrystallization from cyclohexane;

ab. $N^6$-n-butyl-9-[3-(4-phenyl-piperazino)-propyl]-adenine from $N^6$-n-butyl-adenine and 3-(4-phenyl-piperazino)-propyl chloride; yield 67% of theory; m.p. of the dihydrochloride 259°–260° C after recrystallization from methanol;

ac. $N^6$-ethyl-9-{3-[4-(4-fluorophenyl)-piperazino]-propyl}-adenine from $N^6$-ethyl-adenine and 3-[4-(4-fluorophenyl)-piperazino]-propyl chloride; yield 43% of theory; m.p. 130°–132° C after recrystallization from ethyl acetate;

ad. $N^6$-n-butyl-9-{3-[4-(4-fluorophenyl)-piperazino]-propyl}-adenine from $N^6$-n-butyl-adenine and 3-[4-(4-fluorophenyl)-piperazino]-propyl chloride; yield 49% of theory; m.p. 92°–93° C after recrystallization from ethyl acetate.

EXAMPLE 2

$N^6$-n-Propyl-9-[3-(4-phenyl-piperazino)-propyl]-adenine.

a. 6-Chloro-9-[3-(4-phenyl-piperazino)-propyl]-purine used as starting material is prepared in the following manner:

15.4 g (0.1 mole) of 6-chloropurine are dissolved in 75 ml of dimethyl formamide, mixed with 13.8 g (0.1 mole) of potassium carbonate and 23.8 g (0.1 mole) of 3-(4-phenyl-piperazino)-propyl chloride and warmed at 40° C for 6 hours, while stirring. When the reaction is finished, the reaction mixture is mixed with 250 ml of water, extracted with ethyl acetate and the extract dried over anhydrous sodium sulfate. Upon adding excess ethereal hydrogen chloride solution, the dihydrochloride of 6-chloro-9-[3-(4-phenyl-piperazino)-propyl]-purine precipitates out. The yield is 26.4 g (61% of theory) and the compound melts with decomposition at 190°–192° C after recrystallization from isopropanol. The free base can be obtained from this dihydrochloride by treatment with a dilute aqueous solution of sodium hydroxide and extraction with ethyl acetate.

b. 50 ml of n-propylamine are added to a solution of 10.7 g (0.03 mole) of 6-chloro-9-[3-(4-phenyl-piperazino)-propyl]-purine (produced as hereinabove described) in 100 ml of n-propanol, whereafter the reaction mixture is heated under reflux for 5 hours. After standing for 15 hours at ambient temperature, the reaction mixture is evaporated in a vacuum and the residue extracted with ether. After evaporation of the solvent, there are obtained 9.0 g (79% of theory) of crude product, which has a melting point of 64°–66° C. After recrystallization from ether, there are obtained 7.4 g (65% of theory) of $N^6$-n-propyl-9-[3-(4-phenyl-piperazino)-propyl]-adenine, which has a melting point of 67°–68° C.

c. The following compound is prepared in an analogous manner:

$N^6$-isopropyl-9-{3-[4-(4-fluorophenyl)-piperazino]-propyl}-adenine from 6-chloro-9-{3-[4-(4-fluorophenyl)-piperazino]-propyl}-purine and isopropylamine; yield 58% of theory; m.p. of the dihydrochloride 232°–233° C after recrystallization from methanol.

The compounds of the general formula II are known compounds or may be prepared from known compounds in a known manner.

The synthesis of compounds of the general formula III used as starting materials is shown in the following for one representative example:

A mixture of 35.2 g (0.2 mole) of 1-(2-methylphenyl)-piperazine, 31.4 g (0.2 mole) of 1-bromo-3-chloropropane, 40.4 g (0.4 mole) of triethylamine and 100 ml of tetrahydrofurane is refluxed for five hours. After cooling it is filtered, the filtrate is concentrated and the residue is fractionally distilled under vacuum. There are obtained 32.7 g of 3-[4-(2-methyl-phenyl)-piperazino]-propyl chloride (65% of theory) of boiling point 138°–140° C/0.1 mm Hg.

The foregoing compounds can be used as such or they can be converted to salts with pharmacologically acceptable acids.

With respect to the proper dosage and methods of application for the instant compounds, these are comparable to those for the commercially known compound "Fragivix", i.e. 2-ethyl-3-(4'-hydroxybenzoyl)-benzo-furan. The instant compounds make possible comprehensive therapy of acute as well as chronic phlebological and capillary afflications as well as varicose syndromes in mammals. The instant compounds retard reactions leading to edemas and swellings, including those of allergic origin.

The typical daily dosage of 10 to 300 mg results in reducing or eliminating the above afflications, commonly within some days. A preferred dosage is 30–100 mg.

The superior activity of the novel compounds is shown by comparing the inhibition of the passive cutaneous anaphylactic reaction in rats produced by injection of serum containing reaginic antibodies to egg albumin. Diethylcarbamazin, i.e. 1-diethylcarbamoyl-4-methylpiperazine, was used as a comparison compound. Specifically, tests were run as follows:

Serum containing reaginic (IgE-like) antibody to egg albumin was prepared by injecting rats intramuscularly with 0.1 ml of a solution of the antigen (10 mg/ml) in saline together with 0.5 ml of Bordetella pertussis vaccine (Behring; $2 \times 10^{10}$ organisms/ml). 9–14 Days later the animals were bled from the abdominal aorta; the serum was pooled and stored at $-20°$ C until required. The titer of the serum, i.e. the highest dilution inducing passive cutaneous anaphylaxis (PCA) in the rat following a 48-hour latent period, was between 1:8 and 1:32. For use in these experiments the serum was diluted 1:24. The reaginic nature of the antibody was demonstrated by its ability to induce PCA with a latent period in excess of 7 days and also by abolition of its PCA activity by heating it at $56°$ C for 1 hour.

The animals were anesthetized with 2,2-dichloro-1,1-difluoroethyl-methyl ether, sold under the trademark Penthrane, and were sensitized by injecting 0.1 ml of the antiserum into the shaved abdominal flanks. After 48 hours for reaginic PCA, the animals were given an intravenous injection of 1 ml of saline solution containing 0.5% by weight of egg albumin and 0.25% by weight of Evans blue.

After having killed and exsanguinated the animals, the size in square millimeters and the intensity, in arbitary scores, of the resulting blue spot were determined. The product of these two parameters was used to determine the degree of the reaction and the degree of reaction with no active material was taken as the standard against which to measure % inhibition of the anaphylactic reaction.

6 Animals were used per dose level and for control.

In some instances the test material was injected intravenously (i.v.) immediately before the antigen, using a solution in water containing 0.5% HCl and 2% of dimethylformamide, and in other instances intraperitoneally (i.p.) 20 minutes before the antigen, using a suspension in water containing 1% of methylcellulose. The volume of the injection was varied to give the indicated dosage of active material. The results obtained were as follows:

PCA Reaction in Rats Induced by Reaginic Antibodies
(Ovalbumin 2 × cryst. and Bord. pertussis $2 \times 10^{10}$)
Application of the compounds:  i.p. 20 min. before Antigen
(Ovalbumin 5 mg/Animal i.v.)
i.v. immediately before Antigen

| Active Material | Active Material mg/kg | | % Inhibition of PCA | |
|---|---|---|---|---|
| | i.v. | i.p. | i.v. | i.p. |
| Control | 0 | 0 | 0 | 0 |
| Diethylcarbamazin | 60 | 60 | 58 | 19 |
| Ex. 1 (d) | 3 | 3 | 91 | 41 |
| Ex. 1 (q) | — | 3 | — | 57 |
| Ex. 1 (y) | 3 | 3 | 61 | 33 |
| Ex. 1 (ab) | — | 3 | — | 69 |
| Ex. 2 | 3 | 3 | 83 | 59 |

These pharmacological data show that the novel compounds exert a far stronger antianaphylactoid activity than Diethylcarbamazin whether administered intravenously or intraperitoneally.

It will be appreciated that the instant specification and examples are set forth by way of illustration and not limitation, and that various modifications and changes may be made without departing from the spirit and scope of the present invention.

What is claimed is:
1. A $N^6$-substituted-9-[3-(4-phenyl-piperazino)-propyl]-adenine compound of the formula

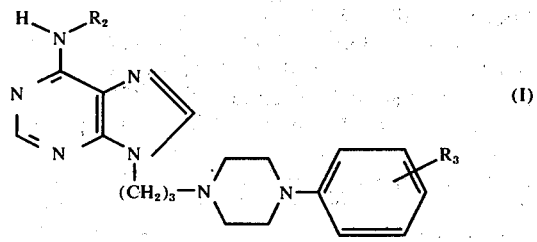

wherein
$R_2$ is lower alkyl, lower alkyl substituted by at least one of phenyl and hydroxyl, lower alkenyl, cycloalkyl of 3 to 6 carbon atoms and phenyl, and
$R_3$ is hydrogen, halogen, lower alkyl or lower alkoxy, or a salt thereof with a pharmacologically compatible acid.

2. A compound according to claim 1 wherein
$R_2$ is alkyl, phenyl-alkyl or hydroxyalkyl wherein the alkyl has 1 to 4 carbon atoms, alkenyl of 2 to 4 carbon atoms, cycloalkyl of 3 to 6 carbon atoms or phenyl, and
$R_3$ is hydrogen, fluorine, chlorine, bromine, or alkyl or alkoxy of 1 to 4 carbon atoms.

3. A compound according to claim 1 wherein such compound is $N^6$-ethyl-9-[3-(4-phenyl-piperazino)-propyl]-adenine or a salt thereof with a physiologically compatible acid.

4. A compound according to claim 1 wherein such compound is $N^6$-n-propyl-9-[3-(4-phenyl-piperazino)-propyl]-adenine or a salt thereof with a physiologically compatible acid.

5. A compound according to claim 1 wherein such compound is $N^6$-methyl-9-{3-[4-(4-fluorophenyl)-piperazino]-propyl}-adenine or a salt thereof with a physiologically compatible acid.

6. A compound according to claim 1 wherein such compound is $N^6$-methyl-9-{3-[4-(4-methylphenyl)-piperazino]-propyl}-adenine or a salt thereof with a physiologically compatible acid.

7. A compound according to claim 1 wherein such compound is $N^6$-n-butyl-9-[3-(4-phenyl-piperazino)-propyl]-adenine or a salt thereof with a physiologically compatible acid.

8. A method of combating edemas and related afflictions in a mammal which comprises administering to said mammal on anti-edematous effective amount of a compound according to claim 1 or a salt thereof with a pharmacologically compatible carried.

9. The method of claim 8 wherein said compound is
$N^6$-ethyl-9-[3-(4-phenyl-piperazino)-propyl]-adenine,
$N^6$-n-propyl-9-[3-(4-phenyl-piperazino)-propyl]-adenine,
$N^6$-methyl-9-{3-[4-(4-fluorophenyl)-piperazino]-propyl}-adenine,
$N^6$-methyl-9-{3-[4-(4-methylphenyl)-piperazino]-propyl}-adenine, or
$N^6$-n-butyl-9-[3-(4-phenyl-piperazino)-propyl]-adenine.

* * * * *